US010905378B1

(12) United States Patent
Ben-Tsur et al.

(10) Patent No.: US 10,905,378 B1
(45) Date of Patent: Feb. 2, 2021

(54) METHOD FOR TREATING GASTROPARESIS USING A VIBRATING INGESTIBLE CAPSULE

(71) Applicant: VIBRANT LTD., Yokneam (IL)

(72) Inventors: Lior Ben-Tsur, Netanya (IL); Camille Morliere, Hadera (IL)

(73) Assignee: VIBRANT LTD, Yokneam (IL)

( * ) Notice: Subject to any disclaimer, the term of this patent is extended or adjusted under 35 U.S.C. 154(b) by 190 days.

(21) Appl. No.: 15/882,329

(22) Filed: Jan. 29, 2018

Related U.S. Application Data

(60) Provisional application No. 62/451,837, filed on Jan. 30, 2017.

(51) Int. Cl.
*A61B 5/00* (2006.01)
*A61B 5/07* (2006.01)

(52) U.S. Cl.
CPC ............ *A61B 5/6861* (2013.01); *A61B 5/073* (2013.01); *A61H 2201/1207* (2013.01)

(58) Field of Classification Search
CPC .............................. A61B 5/6861; A61B 5/073
See application file for complete search history.

(56) References Cited

U.S. PATENT DOCUMENTS

| 3,485,235 | A | 12/1969 | Felson |
| 4,507,115 | A | 3/1985 | Kambara et al. |
| 5,170,801 | A | 12/1992 | Casper et al. |
| 6,632,216 | B2 | 10/2003 | Houzego et al. |
| 6,776,165 | B2 | 8/2004 | Jin |
| 6,929,363 | B2 | 8/2005 | Sakai et al. |
| 6,984,205 | B2 | 1/2006 | Gazdzinski |
| 8,202,697 | B2 | 6/2012 | Holmes |
| 8,518,022 | B2 | 8/2013 | Trovato et al. |
| 8,597,278 | B2 | 12/2013 | Trovato et al. |
| 8,701,677 | B2 | 4/2014 | Duan et al. |
| 9,078,799 | B2 | 7/2015 | Shohat et al. |
| 9,156,169 | B2 | 10/2015 | Duan et al. |
| 9,232,909 | B2 | 1/2016 | Duan et al. |
| 9,532,923 | B2 | 1/2017 | Shohat et al. |
| 9,707,150 | B2 | 7/2017 | Shabbat |
| 2002/0132226 | A1 | 9/2002 | Nair et al. |
| 2003/0020810 | A1 | 1/2003 | Takizawa et al. |
| 2004/0030454 | A1 | 2/2004 | Kim et al. |
| 2004/0253304 | A1 | 12/2004 | Gross et al. |
| 2004/0267240 | A1 | 12/2004 | Gross et al. |

(Continued)

FOREIGN PATENT DOCUMENTS

| CN | 1829466 A | 9/2006 |
| CN | 102743174 A | 10/2012 |

(Continued)

OTHER PUBLICATIONS

ClinicalTrials.gov "Clinical Investigation Plan MA-501" Mar. 15, 2015 (Year: 2015).*

(Continued)

*Primary Examiner* — Samchuan C Yao
*Assistant Examiner* — Matthew Standard
(74) *Attorney, Agent, or Firm* — Momentum IP Group; Marc Van Dyke

(57) ABSTRACT

A method for treating gastroparesis in a subject using a vibrating ingestible capsule ingested by the subject and activated in a targeted zone of the gastrointestinal tract of the subject.

17 Claims, 2 Drawing Sheets

(56) References Cited

U.S. PATENT DOCUMENTS

| | | |
|---|---|---|
| 2005/0058701 A1 | 3/2005 | Gross et al. |
| 2005/0085696 A1 | 4/2005 | Uchiyama et al. |
| 2005/0148847 A1 | 7/2005 | Uchiyama et al. |
| 2005/0177069 A1 | 8/2005 | Takizawa et al. |
| 2006/0169293 A1 | 8/2006 | Yokoi et al. |
| 2006/0276729 A1 | 12/2006 | Reed et al. |
| 2007/0015952 A1 | 1/2007 | Chang et al. |
| 2007/0238940 A1* | 10/2007 | Amirana .............. A61B 5/06 600/302 |
| 2008/0188837 A1 | 8/2008 | Belsky et al. |
| 2008/0275430 A1 | 11/2008 | Belsky et al. |
| 2009/0281380 A1 | 11/2009 | Miller et al. |
| 2009/0306633 A1 | 12/2009 | Trovato et al. |
| 2009/0318841 A1* | 12/2009 | Shohat .............. A61H 23/0263 601/46 |
| 2010/0049012 A1 | 2/2010 | Dijksman et al. |
| 2010/0217079 A1 | 8/2010 | Tichy |
| 2013/0158452 A1* | 6/2013 | Juto .............. A61H 23/02 601/46 |
| 2013/0267788 A1 | 10/2013 | Duan et al. |
| 2015/0011829 A1 | 1/2015 | Wang et al. |
| 2015/0018614 A1 | 1/2015 | Duan et al. |
| 2015/0018615 A1 | 1/2015 | Duan et al. |
| 2015/0073315 A1* | 3/2015 | Shabbat .............. A61B 1/00156 601/46 |
| 2015/0380140 A1 | 12/2015 | Duan et al. |
| 2016/0287058 A1 | 10/2016 | Ye et al. |
| 2016/0310357 A1 | 10/2016 | Duan et al. |
| 2017/0020374 A1 | 1/2017 | Duan et al. |
| 2017/0035407 A1 | 2/2017 | Duan et al. |
| 2017/0035520 A1 | 2/2017 | Duan et al. |
| 2017/0135897 A1 | 5/2017 | Shohat et al. |
| 2017/0273863 A1 | 9/2017 | Shabbat |
| 2017/0296425 A1 | 10/2017 | Duan et al. |
| 2017/0296428 A1 | 10/2017 | Duan et al. |
| 2017/0340242 A1 | 11/2017 | Duan |
| 2018/0055597 A1 | 3/2018 | Duan et al. |
| 2018/0084975 A1 | 3/2018 | Duan et al. |

FOREIGN PATENT DOCUMENTS

| | | |
|---|---|---|
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105411505 A | 3/2016 |
| CN | 205108749 U | 3/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2010503451 A | 2/2010 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2013121276 A1 | 8/2013 |
| WO | 2018055487 A1 | 3/2018 |

OTHER PUBLICATIONS

Smart capsule to target colon diseases, Ben Gruber, Sep. 30, 2015 https://www.reuters.com/article/us-smart-capsule-colon-idUSKCN0RU1ZE20150930.

'Advanced Delivery Devices—IntelliCap: An Intelligent, Electronic Capsule for Oral Drug Delivery & Development', Drug Development & Delivery, Apr. 2013 http://drug-dev.com/advanced-delivery-devices-intellicap-an-intelligent-electronic-capsule-for-oral-drug-delivery-development/.

Machine Translation (by Google Patents) for CN 102743174 published on Oct. 24, 2012.

Machine Translation (by Google Patents) for CN 102743175 published on Oct. 24, 2012.

Machine Translation (by Google Patents) for CN 102743176 published on Oct. 24, 2012.

Machine Translation (by Google Patents) for CN 102813515 published on Dec. 12, 2012.

Machine Translation (by Google Patents) for CN 102860810 published on Jan. 9, 2013.

Machine Translation (by Google Patents) for CN 03222842 published on Jul. 31, 2013.

Machine Translation (by Google Patents) for CN 104898850 published on Sep. 9, 2015.

Machine Translation (by Google Patents) for CN 105025245 published on Nov. 4, 2015.

Machine Translation (by Google Patents) for CN 105079970 published on Nov. 25, 2015.

Machine Translation (by Google Patents) for CN 105411505 published on Mar. 23, 2016.

Machine Translation (by Google Patents) for CN 105939451 published on Sep. 14, 2016.

Machine Translation (by Google Patents) for CN 105942959 published on Sep. 21, 2016.

Machine Translation (by Google Patents) for CN 105996961 published on Oct. 12, 2016.

Machine Translation (by Google Patents) for CN 106056588 published on Oct. 26, 2016.

Machine Translation (by Google Patents) for CN 106097335 published on Nov. 9, 2016.

Machine Translation (by Google Patents) for CN 106137760 published on Nov. 23, 2016.

Machine Translation (by Google Patents) for CN 106204599 published on Dec. 7, 2016.

Machine Translation (by Google Patents) for CN 106373137 published on Feb. 1, 2017.

Machine Translation (by Google Patents) for CN 106923787 published on Jul. 7, 2017.

Machine Translation (by Google Patents) for CN 106934799 published on Jul. 7, 2017.

Machine Translation (by Google Patents) for CN 107174188 published on Sep. 19, 2017.

Machine Translation (by Google Patents) for CN 107233580 published on Oct. 10, 2017.

Machine Translation (by Google Patents) for CN 107240091 published on Oct. 10, 2017.

Machine Translation (by Google Patents) for CN 107375951 published on Nov. 24, 2017.

Machine Translation (by Google Patents) for CN 1829466 published on Sep. 6, 2006.

(56) References Cited

OTHER PUBLICATIONS

Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.
Non-final USTPO action for co-pending U.S. Appl. No. 15/882,283 [action dated Nov. 27, 2019].
Co-pending U.S. Appl. No. 15/882,283, filed Jan. 29, 2018.
Co-pending U.S. Appl. No. 15/882,289, filed Jan. 29, 2018.
Co-pending U.S. Appl. No. 15/882,329, filed Jan. 29, 2018.
Co-pending U.S. Appl. No. 15/882,536, filed Jan. 29, 2018.
Co-pending U.S. Appl. No. 15/882,552, filed Jan. 29, 2018.

\* cited by examiner

METHOD FOR TREATING GASTROPARESIS USING A VIBRATING INGESTIBLE CAPSULE

RELATED APPLICATIONS

The present application gains priority from U.S. Provisional Patent Application No. 62/451,837 filed Jan. 30, 2017 and entitled METHOD FOR TREATING GASTROPARESIS USING A VIBRATING INGESTIBLE CAPSULE, which is incorporated herein by reference as if fully set forth herein.

FIELD OF THE INVENTION

The present invention relates in general to methods of treating gastroparesis, particularly to methods of treating gastroparesis using a vibrating ingestible capsule.

SUMMARY OF THE INVENTION

In accordance with an embodiment of the present invention, there is provided a method of treating gastroparesis in a human subject using a gastrointestinal capsule adapted to transit an alimentary canal of the subject, the capsule having:
a housing;
a battery, disposed within the housing; and
a vibrating agitation mechanism, powered by the battery, the vibrating agitation mechanism adapted such that, in a first vibrating mode of operation, the housing exerts vibrations on an environment surrounding the capsule, the method including:
(a) ingesting the gastrointestinal capsule; and
(b) controlling the vibrating agitation mechanism such that at least a portion of the first vibrating mode of operation occurs when the capsule is disposed within a targeted zone within a gastrointestinal tract of the subject, so as to treat, reduce, or alleviate gastroparesis in the subject.

In some embodiments, the targeted zone includes a section of the gastrointestinal tract of the subject adjacent the pyloric sphincter.

In some embodiments, the targeted zone is in the stomach of the subject.

In some embodiments, the targeted zone is the duodenum of the subject.

In some embodiments, controlling includes pre-setting an activation time delay of the capsule, prior to the ingesting.

In some embodiments, the activation time delay is in the range of 1 second to 5 hours, 1 second to 4 hours, 1 second to 3 hours, 1 second to 2 hours, 1 second to 1 hour, 1 second to 40 minutes, 1 second to 30 minutes, 1 second to 20 minutes, 1 minute to 6 hours, 1 minute to 5 hours, 1 minute to 4 hours, 1 minute to 3 hours, 1 minute to 2 hours, 1 minute to 1 hour, 1 minute to 40 minutes, 1 minute to 30 minutes, 1 minute to 20 minutes, 5 minutes to 6 hours, 5 minutes to 5 hours, 5 minutes to 4 hours, 5 minutes to 3 hours, 5 minutes to 2 hours, 10 minutes to 6 hours, 10 minutes to 5 hours, 10 minutes to 4 hours, 10 minutes to 3 hours, or 10 minutes to 2 hours.

In some embodiments, the subject is a particular subject and wherein the pre-setting of the activation time delay is according to a measured or estimated transit time of chyme along the gastrointestinal tract of the particular subject. In some embodiments, the method further includes, prior to pre-setting the activation time delay, obtaining information relating to the measured or estimated transit time of chyme along the gastrointestinal tract of the particular subject.

In some embodiments, the vibrating agitation mechanism includes at least a radial agitation mechanism adapted, in the first vibrating mode of operation, to exert radial forces on the housing, in a radial direction with respect to a longitudinal axis of the housing, thereby to cause the vibrations of the housing. In some embodiments, the radial agitation mechanism includes unbalanced weight attached to a shaft of an electric motor powered by the battery.

In some embodiments, the vibrating agitation mechanism includes at least an axial agitation mechanism adapted, in the first vibrating mode of operation, to exert axial forces on the housing, in an axial direction with respect to a longitudinal axis of the housing, thereby to cause the vibrations of the housing. In some embodiments, the axial agitation mechanism includes an electric motor powered by the battery and an urging mechanism, associated with, and driven by, the electric motor, the urging mechanism adapted to exert the axial forces. In some embodiments, the urging mechanism is adapted to exert the axial forces in opposite directions. In some embodiments, the urging mechanism is adapted to deliver at least a portion of the axial forces in a knocking mode.

In some embodiments, the vibrating agitation mechanism is adapted in the first vibrating mode of operation, to exert radial forces on the housing in a radial direction with respect to a longitudinal axis of the housing and to exert axial forces on the housing in an axial direction with respect to the longitudinal axis of the housing, thereby to cause the vibrations of the housing.

In some embodiments, the vibrating agitation mechanism includes a radial agitation mechanism adapted to exert the radial forces and a separate axial agitation mechanism adapted to exert the axial forces.

In some embodiments, the vibrating agitation mechanism includes a single agitation mechanism adapted to exert the radial forces and the axial forces.

In some embodiments, the vibrating mode of operation including a plurality of cycles, each of the cycles including a vibration duration followed by a repose duration, wherein the housing exerts the vibrations during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, or 4 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours. In some embodiments, the cumulative duration is dependent on properties of the battery.

In some embodiments, the vibrating agitation mechanism is configured such that a net force exerted by the housing on the environment is in the range of 50 grams-force to 600 grams-force.

In some embodiments, the vibrating agitation mechanism is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, controlling of the vibrating agitation mechanism is effected so as to effect a mechanical stimulation of the wall of the gastrointestinal tract in the targeted zone.

In some embodiments, the subject is a subject who has experienced nausea at least 25% of the time for at least two weeks preceding treatment.

In some embodiments, the subject is a subject who has experienced vomiting after at least one meal per day or after 25% of the meals for at least two weeks preceding treatment.

In some embodiments, the subject is a subject who has experienced a feeling of fullness after eating ten bites or fewer in at least 50% of the meals for at least two weeks preceding treatment.

In some embodiments, the subject is a subject who has experienced heart burn or acid reflux at least 25% of the time for at least two weeks preceding treatment.

In some embodiments, ingesting and controlling together form a treatment session, and wherein the method includes administering to the subject at least one the treatment session.

In some embodiments, administering to the subject at least one treatment session includes administering to the subject a plurality of treatment sessions.

In some embodiments, administering a plurality of treatment sessions includes administering at least one the treatment session per week, over a treatment period of at least two weeks, at least at least three weeks, at least four weeks, at least five weeks, at least six weeks, or at least eight weeks.

In some embodiments, administering at least one treatment session per week includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

BRIEF DESCRIPTION OF THE FIGURES

The foregoing discussion will be understood more readily from the following detailed description of the invention, when taken in conjunction with the accompanying FIGS. 1-2, in which.

DESCRIPTION OF THE PREFERRED EMBODIMENTS

Figure 1:
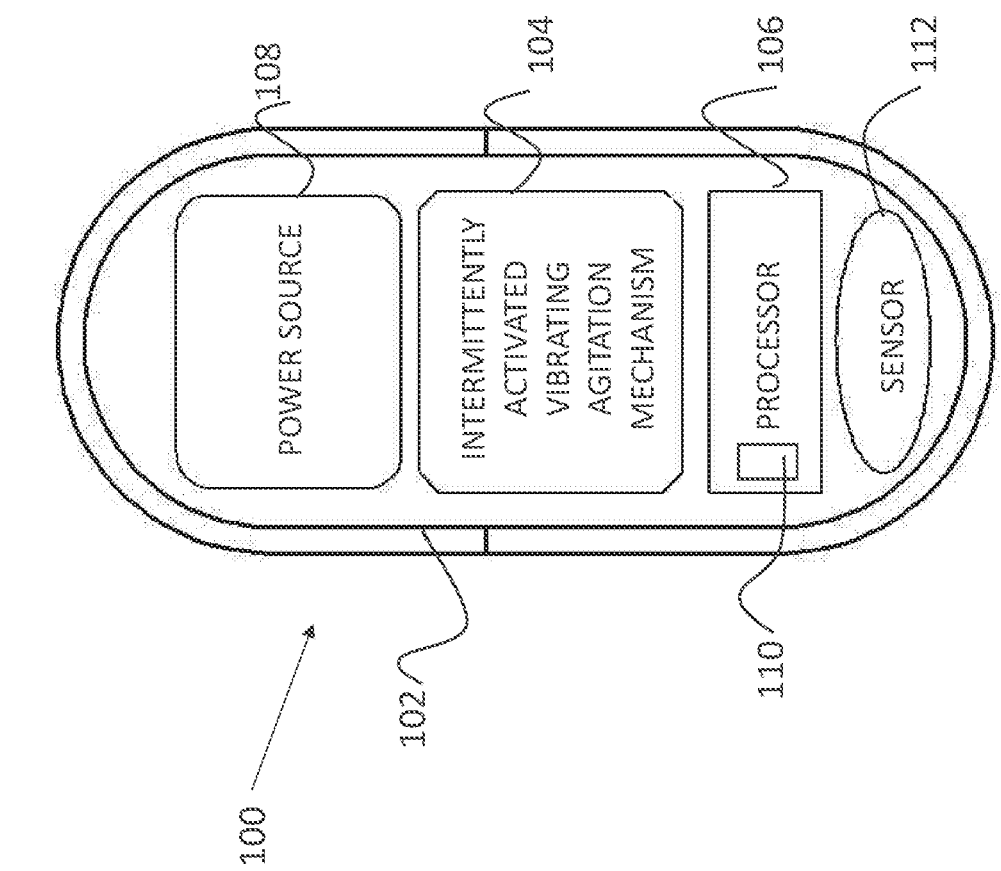
FIG. 1 is a schematic block diagram of an vibrating ingestible capsule for treating gastroparesis in a human subject according to an embodiment of the present invention.

The principles of the inventive method of treating gastroparesis in a human subject using a vibrating ingestible capsule, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

We have discovered a method for treating gastroparesis in a human using an ingestible vibrating gastrointestinal capsule. We have found that when a human subject, suffering from gastroparesis, ingests a vibrating gastrointestinal capsule according to a particular treatment schedule, and the capsule vibrates within the gastrointestinal tract of the subject, and specifically within the stomach of the subject, in accordance with a vibration protocol, the gastroparesis is reduced or alleviated.

Methods of treating constipation using a vibrating gastrointestinal capsule are known in the art, and are described, for example, in U.S. Pat. No. 9,707,150. We have surprisingly found that similar vibrating gastrointestinal capsules are also useful in treating gastroparesis, which is a condition of the stomach, unlike constipation which is typically the result of an intestinal condition.

For the purposes of this application, the term "subject" relates to a human.

For the purposes of this application, the term "vibrating ingestible capsule" relates to an ingestible capsule adapted to at least intermittently vibrate, for a cumulative duration of at least one minute, in accordance with a vibration protocol of the capsule.

For the purposes of this application, the term "intermittently activated vibrating agitation mechanism" refers to a vibration engine that vibrates and is operative at certain times, and does not vibrate at other times, the activation times being selected by a processor or other control unit controlling the vibration engine.

For the purposes of this application, the term "vibration protocol" relates to a protocol specifying vibration parameters of an intermittently activated vibrating agitation mechanism of a vibrating ingestible capsule. Typically, the vibration protocol relates to an activation delay for initiating vibration (a duration between activation of the capsule and the first activation of the vibration engine), a vibration rate (number of vibration cycles per hour), a vibration duration and a repose duration for each vibration cycle, a vibration frequency, an amount of force exerted by the vibrations, and the like.

For the purposes of this application, the term "treatment procedure" relates to parameters of a treatment utilizing vibrating ingestible capsules, which are typically defined by a treating physician or medical practitioner. For example, the treatment procedure may include the number of capsule to be taken within a specific time duration (e.g. 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a subject with a vibrating ingestible capsule, and includes the treatment procedure as well as the vibration protocol to be used for treating the subject.

For the purpose of the application, the term "transit time" relates to the amount of time it takes for a quanta of food or chyme to move a predetermined distance along the gastrointestinal tract of a particular subject. For example, the transit time may be the amount of time it takes a quanta of chyme to move from the duodenum to the rectum of the subject. The term transit time may relate to a transit time along the whole gastrointestinal tract, from the subject ingesting a food till chyme of that food reaches the rectum, or may relate to transit time within a segment of the gastrointestinal tract, such as the time it takes food from swallowing thereof till it passes from the stomach into the duodenum.

For the purpose of this application, the terms "treat gastroparesis" and "reduce gastroparesis" relate to providing a treatment, such that by the end of the treatment period, which may be at least 2 weeks, at least 3 weeks, at least 4 weeks, at least 6 weeks, or at least 8 weeks, there is an improvement of at least 5%, at least 10%, at least 15%, or at least 20% in at least one symptom of gastroparesis over the entire treatment period. For example, a subject being nauseous at least 5% less of the time, a subject having at least 5% fewer vomiting episodes per week, a marker showing that at least 5% more food passed from the stomach into the intestine of the subject than had passed before initiation of treatment, and/or a marker showing at least 5% more contraction of the pyloric sphincter or in the vicinity of the pyloric sphincter than were measured prior to initiation of treatment, a subject having heart-burn or acid reflux at least 5% less of the time, or a subject able to consume at least 5% more food per day, are all considered successful treatment of gastroparesis or reduction of gastroparesis.

For the purpose of this application, the term "alleviate gastroparesis" relates to providing a treatment such that gastroparesis ceases to be a chronic or persistent condition occurring on a daily or weekly basis, such that food is pumped from the stomach into the intestine on a regular basis.

Referring now to the drawings, FIG. 1 is a schematic block diagram of an ingestible vibrating gastrointestinal capsule for treating gastroparesis in a human subject according to embodiments of the present invention.

As seen in FIG. 1, vibrating ingestible capsule 100 includes a capsule housing or shell 102, having disposed therein a vibrating agitation mechanism 104 adapted to be intermittently activated, a processor 106 adapted to control operation of the vibrating agitation mechanism 104, and at least one power source 108 providing power to vibrating agitation mechanism 104 and processor 106. In some embodiments, the processor is functionally associated with a timer 110. In some embodiments, capsule 100 further includes at least one sensor 112, functionally associated with processor 106. The at least one sensor 112 may be adapted to sense at least one parameter within capsule 100 or in an environment of capsule 100, and may include a temperature sensor, a moisture sensor, a pH sensor, or any other suitable sensor.

Power source 108 may be any suitable power source, such as, for example, one or more alkaline or silver oxide batteries, primary batteries, rechargeable batteries, capacitors and/or super capacitors. In some embodiments, the power source may be a zinc-manganese dioxide alkaline battery, such as a AG3/LR41 button cell, commercially available from Daly-Station Battery Limited of Shenzhen Guandong, P.R. China.

Intermittently activated vibrating agitation mechanism 104 is adapted to have a vibration mode of operation and a rest mode of operation. In the vibration mode of operation, intermittently activated vibrating agitation mechanism 104 is adapted to exert forces on capsule housing 102, such that capsule housing 102 exerts vibrations on an environment surrounding capsule 100.

In some embodiments, intermittently activated vibrating agitation mechanism 104 may include a radial agitation mechanism adapted to exert radial forces on the capsule housing 102, in a radial direction with respect to a longitudinal axis of housing 102. For example, the radial agitation mechanism may include an unbalanced weight attached to a shaft of an electric motor powered by said battery, substantially as described in U.S. Pat. No. 9,707,150, which is incorporated by reference for all purposes as if fully set forth herein.

In some embodiments, intermittently activated vibrating agitation mechanism 104 may include an axial agitation mechanism adapted to exert radial forces on the capsule housing 102, in an axial direction with respect to a longitudinal axis of housing 102. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitation mechanism 104 on capsule housing 102 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitation mechanism 104.

In some embodiments, intermittently activated vibrating agitation mechanism 104 may be a coin type eccentric vibration motor, such as a coin-type motor having the Product Part No. C0834L-066332017-2001 commercially available from Ineed HK Limited of Kowloon, Hong-Kong.

In the vibrating mode of operation, intermittently activated vibrating agitation mechanism 104 is adapted to have a plurality of vibration cycles, where each cycle includes a vibration duration followed by a repose duration. Forces are exerted by vibrating agitation mechanism 104 on capsule housing 102 only during the vibration duration, and as such capsule housing 102 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 108.

It will be appreciated by persons skilled in the art that the vibration mode of operation may be intermittent, or interrupted, such that vibrating agitation mechanism 104 is operative in the vibration mode for a first duration, for example 30 minutes, then does not vibrate, or have any vibration cycles, for a second duration, for example 1 hour, and then is operative in the vibration mode and has vibration cycles for a third duration, for example two hours. The cumulative duration relates to the sum of all durations during which the vibrating agitation mechanism 104 was operative in the vibration mode and included vibration cycles, including the vibration duration and the repose duration of these vibration cycles.

In some embodiments, vibrating agitation mechanism 104 is configured to exert forces on capsule housing 102, such that a net force exerted by capsule housing 102 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitation mechanism 104 is configured to exert said forces on capsule housing 102 to attain a capsule housing 102 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source and of the vibrating agitation mechanism.

It will be further appreciated that a specific capsule may be controlled by the processor such that different vibrational frequencies may be attained and/or different net forces may be exerted, by the capsule in different vibration cycles of the capsule. Due to the natural distinction between subjects, use of multiple different parameters in different vibration cycles of a single capsule would allow the capsule to successfully treat multiple subjects, even if the personal optimal treatment for those subjects is not the same, as there is a higher chance that in at least some of the vibration cycles the activation parameters of the capsule would reach, or be close to, the optimal parameters for each specific subject.

Processor 106 is adapted to control the operation of intermittently activated vibrating agitation mechanism 104. Such control may include control of any one or more of the force applied by the vibrating agitation mechanism, the vibrational frequency reached, the times in which vibrating agitation mechanism 104 operates in the vibration mode of operation, the vibration duration of each vibration cycle, the repose duration of each vibration cycle, the vibration cycle duration, and cumulative vibration duration of the vibrating agitation mechanisms.

In some embodiments, processor 106 is adapted to wait for a pre-set activation time delay following activation of capsule 100 and prior to initiation of the vibration mode of operation of vibration agitation mechanism 104. The activation time delay may be any suitable time delay, and may be dependent on portions of the gastrointestinal tract in which it is desired that the capsule will operate.

For example, for treatment of gastroparesis, when it is desired that the capsule operate, or vibrate, within the stomach of the subject or near the pyloric sphincter, the activation time delay may be in the range of 1 second to 5 hours, 1 second to 4 hours, 1 second to 3 hours, 1 second to 2 hours, 1 second to 1 hour, 1 second to 40 minutes, 1 second to 30 minutes, 1 second to 20 minutes, 1 minute to 6 hours, 1 minute to 5 hours, 1 minute to 4 hours, 1 minute to 3 hours, 1 minute to 2 hours, 1 minute to 1 hour, 1 minute to 40 minutes, 1 minute to 30 minutes, 1 minute to 20 minutes, 5 minutes to 6 hours, 5 minutes to 5 hours, 5 minutes to 4 hours, 5 minutes to 3 hours, 5 minutes to 2 hours, 10 minutes to 6 hours, 10 minutes to 5 hours, 10 minutes to 4 hours, 10 minutes to 3 hours, or 10 minutes to 2 hours.

In some embodiments, processor 106 is adapted to receive information relating to the desired vibration protocol from a control unit (not shown), prior to ingestion of the capsule or to activation thereof. For example, the information may be remotely transmitted from the control unit to processor 106, for example using a short range wireless communication method. In some embodiments, the information is transmitted as a list of vibration parameters for effecting the vibration protocol. In some embodiments, the information is transmitted as executable code for effecting the vibration protocol.

In some embodiments, the information includes one or more of a desired activation time delay, a desired number of vibration cycles, a desired vibration duration in each vibration cycle, a desired repose duration in each vibration cycle, a desired cumulative vibration duration, and the like.

In some embodiments, processor 106, or a timer associated therewith, is adapted to be activated by the control unit prior to ingestion of capsule 100. In some embodiments, activation is carried out by sending a signal to processor 106, for example using a short range wireless communication protocol. In some embodiments, the activation signal activates the timer to immediately begin effecting the vibration protocol. In some embodiments, the at least one sensor 108 is adapted to identify ingestion of the capsule, and processor 106 is adapted to begin effecting the vibration protocol immediately following identification of ingestion of capsule 100.

In some embodiments, processor 106 is adapted to control vibrating agitation mechanism 104 so that the capsule applies forces to an environment thereof to effect a mechanical stimulation of the wall of the gastrointestinal tract of the subject in a targeted zone.

Figure 2:
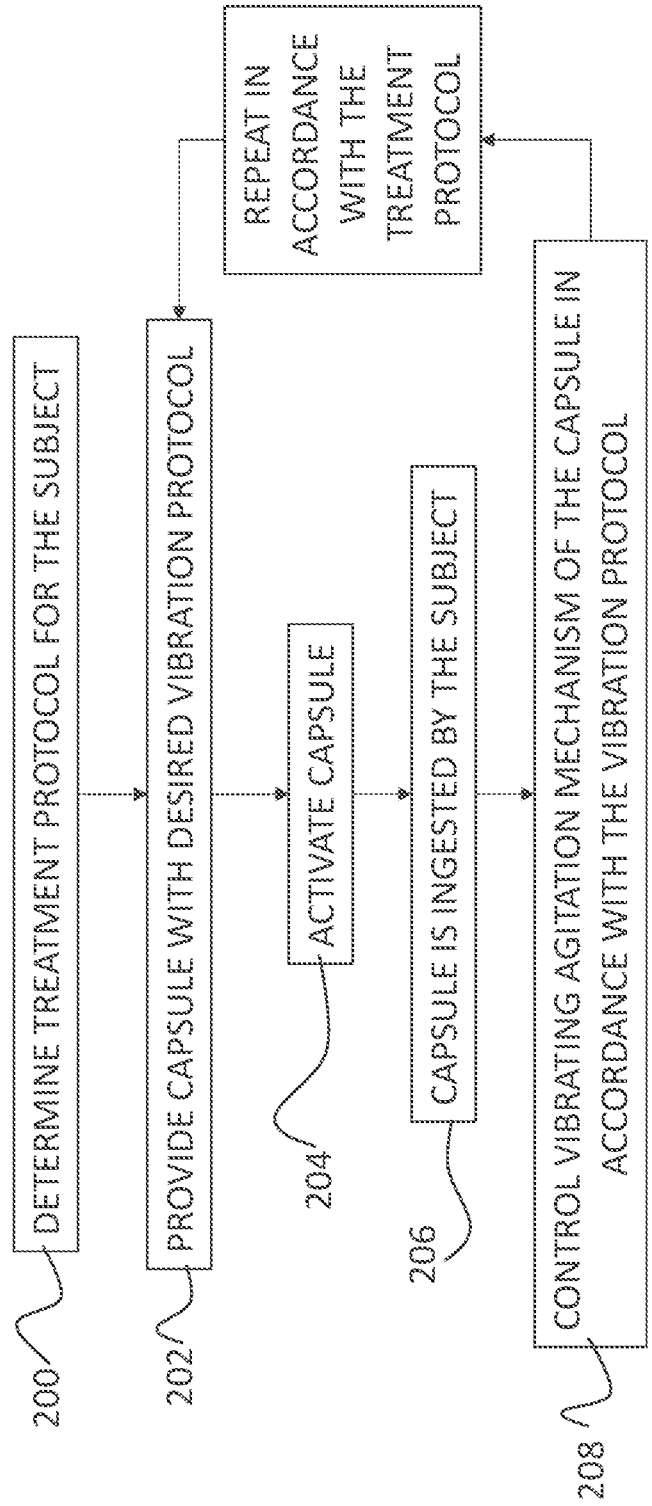
FIG. 2 is a schematic flowchart of a method for treating gastroparesis in a human subject according to the present invention, the treatment being based one use of an ingestible vibrating gastrointestinal capsule.

Reference is now additionally made to FIG. 2, which is a schematic flowchart of a method for treating gastroparesis in a human subject according to the present invention, the treatment being based one use of an ingestible vibrating gastrointestinal capsule such as capsule 100 of FIG. 1.

As seen at step 200, initially the treatment protocol for the subject is set or determined, for example by a treating physician or medical practitioner. The treatment protocol may indicate the number of treatment sessions per week or per other time duration, the time of day at which a capsule should be ingested, a targeted zone in which the capsule should be operative, and/or may indicate the vibration protocol of the capsule. For treatment of gastroparesis, the targeted zone may within the stomach of the subject, or in an area in the vicinity of the pyloric sphincter.

At step 202, the processor 106 of an ingestible capsule 100 may optionally receive, or be programmed with, a desired vibration protocol, in accordance with the treatment protocol determined at step 200. In some embodiments, such programming of the desired vibration protocol is effected by a control unit. For example, the programming may include remotely transmitting the desired vibration protocol from the control unit to processor 106, for example using a short range wireless communication method. In some embodiments, the desired vibration protocol is transmitted as a list of vibration parameters for effecting the vibration protocol. In some embodiments, the desired vibration protocol is transmitted as executable code for effecting the vibration protocol.

In some embodiments, step 202 includes pre-setting of an activation time delay for activation of the capsule. In some embodiments, However, in some embodiments, ingestible capsule 100 may be pre-programmed, for example with a default vibration protocol or with a pre-set protocol, in which case step 202 may have been previously executed, e.g., by the capsule manufacturer.

The vibration protocol pre-set or programmed into capsule 100, and specifically the activation time delay of the capsule, is selected to effect vibration of capsule 100 when the capsule will be located in a targeted zone within the gastrointestinal tract of the subject. In some embodiments, the targeted zone is defined in the treatment protocol determined at step 200.

In some embodiments, the targeted zone is a section of the small intestine, such as a section of the duodenum.

In other embodiments the targeted zone is within the stomach of the subject.

As mentioned above, for treatment of gastroparesis the targeted zone is within the stomach of the subject or adjacent the pyloric sphincter. In such embodiments, the activation time delay is selected to be in the range of 1 second to 5 hours, 1 second to 4 hours, 1 second to 3 hours, 1 second to 2 hours, 1 second to 1 hour, 1 second to 40 minutes, 1 second to 30 minutes, 1 second to 20 minutes, 1 minute to 6 hours, 1 minute to 5 hours, 1 minute to 4 hours, 1 minute to 3 hours, 1 minute to 2 hours, 5 minutes to 6 hours, 5 minutes to 5 hours, 5 minutes to 4 hours, 5 minutes to 3 hours, 5 minutes to 2 hours, 10 minutes to 6 hours, 10 minutes to 5 hours, 10 minutes to 4 hours, 10 minutes to 3 hours, or 10 minutes to 2 hours.

In some embodiments, the selected activation time delay is selected according to a measured or estimated transit time of chyme along the gastrointestinal tract of the subject being treated, and specifically out of the subject's stomach. In some such embodiments, information relating to the measured or estimated transit time of chyme is collected prior to step 202.

The capsule is activated for use at step 204. In some embodiments, activation is performed automatically when the capsule receives the vibration protocol, at step 202. In other embodiments, such as in embodiments in which the vibration protocol is pre-set, the capsule may be explicitly activated, such as by receipt of an activation signal from the control unit or by sensors within the capsule sensing that the capsule has been ingested. Activation of the capsule results in activation of the timer associated with the processor 106, and is the start of the activation time delay.

Following activation of capsule 100, or together therewith, capsule 100 is ingested by the subject, and begins to travel through the gastrointestinal tract of the subject, as seen at step 206.

At step 208, while capsule 100 is travelling in the gastrointestinal tract together with the food/chyme therein, processor 106 controls the vibrating agitation mechanism 104 in accordance with the vibration protocol, so that vibrating agitation mechanism 104 is in the vibrating mode of operation when the capsule is disposed in the targeted zone.

Operation of vibrating agitation mechanism 104 in the vibrating mode of operation effects vibration of capsule housing 102, as described hereinabove, such that the housing exerts vibrations on the environment surrounding the capsule in the targeted zone. Specifically, vibration of capsule housing 102 may be intended to effect a mechanical stimulation of the wall of the gastrointestinal tract in the targeted zone.

A treatment session as defined in steps 202 to 208 may be repeatedly administered to the subject as specified in the treatment protocol for the subject, determined or obtained at step 200. In some embodiments, the treatment protocol includes administering a plurality of treatment sessions to the subject. In some embodiments, the treatment protocol includes administering at least one treatment session to the subject per week, over a treatment period of at least two weeks, at least at least three weeks, at least four weeks, at least five weeks, at least six weeks, or at least eight weeks.

In some embodiments, the treatment protocol includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

The subject may be any suitable subject suffering from gastroparesis. The gastroparesis may be caused by any of a number of underlying conditions, such as diabetes, injury to the vagus nerve, Parkinson's disease, multiple sclerosis, amyloidosis, scleroderma, substance abuse, and/or medications taken by the subject.

In some embodiments, the subject is a subject who has experienced nausea at least 25% of the time for at least two weeks preceding treatment.

In some embodiments, the subject is a subject who has experienced vomiting after at least one meal per day or after 25% of the meals for at least two weeks preceding treatment.

In some embodiments, the subject is a subject who has experienced a feeling of fullness after eating ten bites or fewer in at least 50% of the meals for at least two weeks preceding treatment.

In some embodiments, the subject is a subject who has experienced heart burn or acid reflux at least 25% of the time for at least two weeks preceding treatment.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method of treating gastroparesis in a human subject suffering from gastroparesis, the method comprising:
   (a) providing, to the human subject suffering from gastroparesis, a vibrating gastrointestinal capsule adapted to transit an alimentary canal of a human, said vibrating gastrointestinal capsule having:
      a housing;
      a battery, disposed within said housing; and
      a vibrating agitation mechanism, powered by said battery, said vibrating agitation mechanism adapted such that, in a first vibrating mode of operation, said housing exerts vibrations on an environment surrounding said capsule, wherein, in said first vibrating mode of operation, said vibrating agitation mechanism is configured to exert the vibrations within a range of 150 Hz to 500 Hz;
   (b) ingesting, by the human subject suffering from gastroparesis, said vibrating gastrointestinal capsule, to treat said gastroparesis; and
   (c) controlling said vibrating agitation mechanism such that said first vibrating mode of operation occurs when said capsule is disposed within a targeted zone within a gastrointestinal tract of the subject, so as to treat, reduce, or alleviate gastroparesis in said subject, wherein said targeted zone is the stomach of the human subject.

2. The method of claim 1, said controlling including pre-setting an activation time delay of said capsule, prior to said ingesting.

3. The method of claim 2, wherein the subject is a particular subject and wherein said pre-setting of said activation time delay is according to a measured or estimated transit time of chyme along said gastrointestinal tract of said particular subject.

4. The method of claim 3, further comprising, prior to said pre-setting of said activation time delay, obtaining information relating to said measured or estimated transit time of chyme along said gastrointestinal tract of said particular subject.

5. The method of claim 1, wherein said controlling of said vibrating agitation mechanism is effected so as to effect a mechanical stimulation of the wall of said gastrointestinal tract in said targeted zone.

6. The method of claim 1, wherein the subject is a subject who has reported experiencing nausea at least 25% of the time for at least two weeks preceding treatment.

7. The method of claim 1, wherein the subject is a subject who has experienced vomiting after at least one meal per day or after 25% of the meals for at least two weeks preceding treatment.

8. The method of claim 1, wherein the subject is a subject who has experienced a feeling of fullness after eating ten bites or fewer in at least 50% of the meals for at least two weeks preceding treatment.

9. The method of claim 1, wherein the subject is a subject who has reported experiencing heart burn or acid reflux at least 25% of the time for at least two weeks preceding treatment.

10. The method of claim 1, wherein said subject suffers from at least one of:
    diabetes;
    injury to the vagus nerve;
    Parkinson's disease;
    multiple sclerosis;
    amyloidosis;
    scleroderma;
    substance abuse; and
    side effects of medications taken by the subject.

11. The method of claim 1, wherein said ingesting and controlling together form a treatment session, and wherein said method includes administering to the subject at least one said treatment session.

12. The method of claim 11, wherein said administering to the subject at least one treatment session includes administering to the subject a plurality of treatment sessions.

13. The method of claim 12, wherein said administering a plurality of treatment sessions includes administering at least one said treatment session per week, over a treatment period of at least two weeks.

14. The method of claim 13, wherein said administering at least one treatment session per week includes administering 1 to 7 treatment sessions per week.

15. A method of treating gastroparesis in a human subject suffering from gastroparesis, the method comprising:
    (a) providing, to the human subject suffering from gastroparesis, a vibrating gastrointestinal capsule adapted to transit an alimentary canal of a human, said vibrating gastrointestinal capsule having:
       a housing;
       a battery, disposed within said housing; and
       a vibrating agitation mechanism, powered by said battery, said vibrating agitation mechanism adapted such that, in a first vibrating mode of operation, said housing exerts vibrations on an environment surrounding said capsule;
    (b) ingesting, by the human subject suffering from gastroparesis, said vibrating gastrointestinal capsule, to treat said gastroparesis; and (c) controlling said vibrating agitation mechanism such that said first vibrating mode of operation occurs when said capsule is disposed within a targeted zone within a gastrointestinal tract of the subject and such that in said first vibrating mode of operation said vibrating agitation mechanism is configured to exert the vibrations within a range of 150 Hz to 500 Hz, so as to treat, reduce, or alleviate gastroparesis in said subject,
wherein said targeted zone is in the small intestine of the human subject.

16. The method of claim 15, wherein said targeted zone is the duodenum of the human subject.

17. The method of claim 15, wherein said targeted zone is a section of the small intestine adjacent the pyloric sphincter of the human subject.

\* \* \* \* \*